US010299767B2

(12) United States Patent
Williams et al.

(10) Patent No.: US 10,299,767 B2
(45) Date of Patent: May 28, 2019

(54) SAMPLE COLLECTION APPARATUS

(71) Applicant: ALPHA-TEC SYSTEMS, INC., Vancouver, WA (US)

(72) Inventors: Richard O. Williams, Vancouver, WA (US); Mark Williams, Vancouver, WA (US); John Kempke, Vancouver, WA (US)

(73) Assignee: Alpha-Tec Systems, Inc., Vancouver, WA (US)

( * ) Notice: Subject to any disclaimer, the term of this patent is extended or adjusted under 35 U.S.C. 154(b) by 483 days.

(21) Appl. No.: 14/964,304

(22) Filed: Dec. 9, 2015

(65) Prior Publication Data

US 2016/0338678 A1 Nov. 24, 2016

Related U.S. Application Data

(60) Provisional application No. 62/164,452, filed on May 20, 2015.

(51) Int. Cl.
*A61B 5/00* (2006.01)
*A61B 10/00* (2006.01)
*A61B 10/02* (2006.01)

(52) U.S. Cl.
CPC ...... *A61B 10/0038* (2013.01); *A61B 10/0045* (2013.01); *A61B 10/0051* (2013.01); *A61B 10/02* (2013.01); *A61B 2010/0074* (2013.01); *A61B 2010/0208* (2013.01)

(58) Field of Classification Search
CPC . A61B 10/02; A61B 10/0038; A61B 10/0045; A61B 10/0051; A61B 2010/0216

USPC .................................. 600/569, 570, 572
See application file for complete search history.

(56) References Cited

U.S. PATENT DOCUMENTS

| | | | |
|---|---|---|---|
| 4,735,905 A | 4/1988 | Parker | |
| 4,842,826 A | 6/1989 | Guala | |
| 5,624,554 A | 4/1997 | Faulkner et al. | |
| 6,171,259 B1 * | 1/2001 | Fisher | A61B 10/0038 374/E13.002 |
| 6,358,474 B1 | 3/2002 | Dobler et al. | |
| 7,141,033 B2 | 11/2006 | Kanjilal et al. | |
| 7,284,900 B2 | 10/2007 | Mayer | |
| 7,323,144 B2 | 1/2008 | Arai et al. | |
| 7,374,054 B2 | 5/2008 | Brockwell | |
| 7,377,027 B2 | 5/2008 | Mayer | |
| 7,413,551 B2 * | 8/2008 | Decker | A61B 10/0045 600/569 |
| 7,648,681 B2 | 1/2010 | Meyer et al. | |
| 7,767,448 B2 * | 8/2010 | Yong | A61B 10/0045 435/309.1 |
| 7,771,662 B2 | 8/2010 | Pressman et al. | |

(Continued)

FOREIGN PATENT DOCUMENTS

WO 2005072620 A1 8/2005

*Primary Examiner* — Max F Hindenburg
(74) *Attorney, Agent, or Firm* — McCoy Russell LLP

(57) ABSTRACT

The present disclosure describes a sample collection apparatus for collection of biological samples, such as fecal material. The sample collection apparatus includes at least one coupling mechanism to couple a sample collection device to a cap, and includes at least one release mechanism to release at least a part of the sample collection device from the cap. The sample collection device in a first configuration is coupled to the cap and in a second configuration is displaced from the cap.

18 Claims, 14 Drawing Sheets

(56) References Cited

U.S. PATENT DOCUMENTS

| | | |
|---|---|---|
| 7,807,476 B2 | 10/2010 | Pressman et al. |
| 7,850,922 B2 | 12/2010 | Gallagher et al. |
| 7,854,895 B2 | 12/2010 | Gallagher et al. |
| 7,908,935 B2 | 3/2011 | Hasegawa et al. |
| 9,027,420 B1 * | 5/2015 | Ward ........................ G01N 1/02 73/864.71 |
| 9,138,747 B2 * | 9/2015 | Williams ............ A61B 10/0045 |
| 9,732,376 B2 * | 8/2017 | Oyler ................. A61B 10/0051 |
| 2005/0252820 A1 | 11/2005 | Sanchez-Felix et al. |
| 2007/0167900 A1 | 7/2007 | Kanjilal et al. |
| 2007/0287193 A1 | 12/2007 | Pressman et al. |
| 2008/0209709 A1 | 9/2008 | Mayer |
| 2013/0243669 A1 | 9/2013 | Baron et al. |

* cited by examiner

SAMPLE COLLECTION APPARATUS

FIELD OF INVENTION

The present description relates to a sample collection apparatus for biological samples.

BACKGROUND

Analysis of biological samples, such as fecal material, requires appropriate collection of the biological sample by a sample collection device and transferring the sample into a sample specimen jar. Current practice involves collecting a sample using a sample collection device integrated to a cap, the cap configured to couple to a sample specimen jar. The sample collection device with the sample may be introduced into the specimen jar and the integrated cap may be coupled to the sample specimen jar. During sample retrieval from the sample specimen jar for further analysis, including in automated systems, the cap with the integrated sample collection device may be uncoupled from the specimen jar and held aside, which may result in dripping of residual sample from the sample collection device into the surrounding environment. The dripping of the sample from the sample collection device may contaminate the contact environment, including the equipment and the operator, with biohazardous constituents of the sample.

One of the approaches to mitigate the problem of sample dripping from a sample collection device removed from a sample specimen jar is to break off the tip of the sample collection device and leave the broken tip of the sample collection device in the sample specimen jar. In one example, upon uncoupling of a cap with an integrated sample collection device from a sample specimen jar, a tip of the sample collection device may be manually broken off from the sample collection device. The broken off tip of the sample collection device may remain at the bottom of the sample specimen jar while the cap is held aside while sample is being retrieved from the sample specimen jar.

The inventors herein have recognized problems with the above mentioned sample collection device, including the presence of the broken tip of the sample collection device at the bottom of the specimen jar that may interfere with subsequent sample retrieval from the specimen jar. Additionally, breaking the tip of the sample collection device into the sample specimen jar may increase the risk of contamination due to splashing of the sample during the breaking process.

To minimize sample dripping from a sample collection device during retrieval of sample from a sample specimen jar, the inventors propose a sample collection device that may be releasable from a cap configured to couple to a sample specimen jar.

One example of the sample collection apparatus may include a cap and a sample collection device having a first configuration and a second configuration, where in the first configuration the sample collection device is coupled to the cap and in the second configuration, at least a portion of the sample collection device is released from the cap. In an example, a coupling mechanism may position the sample collection device in the first configuration. The coupling mechanism may include at least one threaded portion on the sample collection device mating with a complementary threaded portion on the cap. Another example of the coupling mechanism may include a socket in the cap receiving the sample collection device. A displacement mechanism may position the sample collection device in the second configuration. In one example, the displacement mechanism may include a mechanical actuator on the cap. In another example, the displacement mechanism may include a cutaway portion on the sample collection device. The sample collection device may include a shank terminating in a scoop.

In another example, the sample collection device coupled to the cap may be adjustable to a first position for sample collection and a second position relative to the cap, where in the first position the cap is spaced apart from a cutaway portion of the sample collection device and in the second position the cutaway portion of the sample collection device may be positioned above a top side of the cap. In one example, when the sample collection device is adjusted in the second position, the cutaway portion of the sample collection device may be adjoining the top side of the cap. In another example, when the sample collection device is adjusted in the second position, the cap may shroud at least a portion of a sample collection end of the sample collection device. When the sample collection device is adjusted in the second position, at least a portion of the sample collection device may be released from the cap.

One example method of using the above described sample collection apparatus, may include collecting a sample using a sample collection device coupled to a cap, introducing the sample collection device with the sample into a sample specimen jar, releasing the sample collection device from the cap, and retaining the cap on the sample specimen jar. The method may include releasing only a portion of the sample collection device from the cap. Releasing the sample collection device from the cap may be done outside the sample specimen jar or inside the sample specimen jar. In one example, releasing the sample collection device from the cap may be done after coupling the cap to the sample specimen jar.

Thus, a sample collection apparatus including a sample collection device releasable from a cap may prevent dripping of residual sample from the sample collection device upon uncoupling of the cap from a sample specimen jar, reducing contamination of the contact environment and the operator.

DETAILED DESCRIPTION

Figure 1:
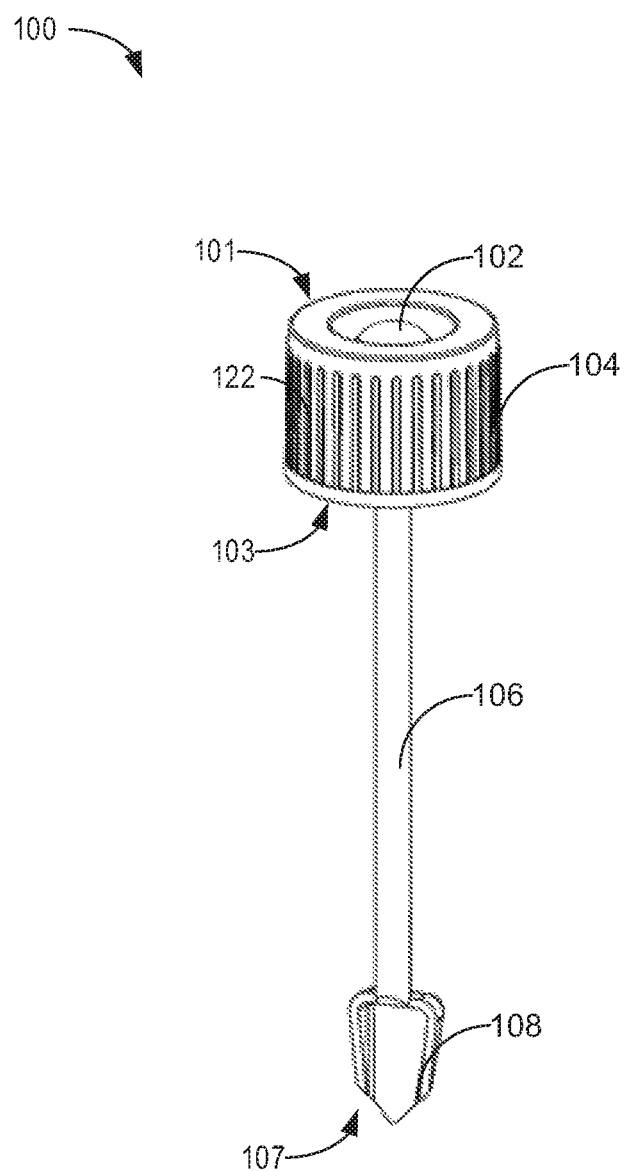
FIG. 1 shows a perspective view of a sample collection apparatus.
Figure 2:
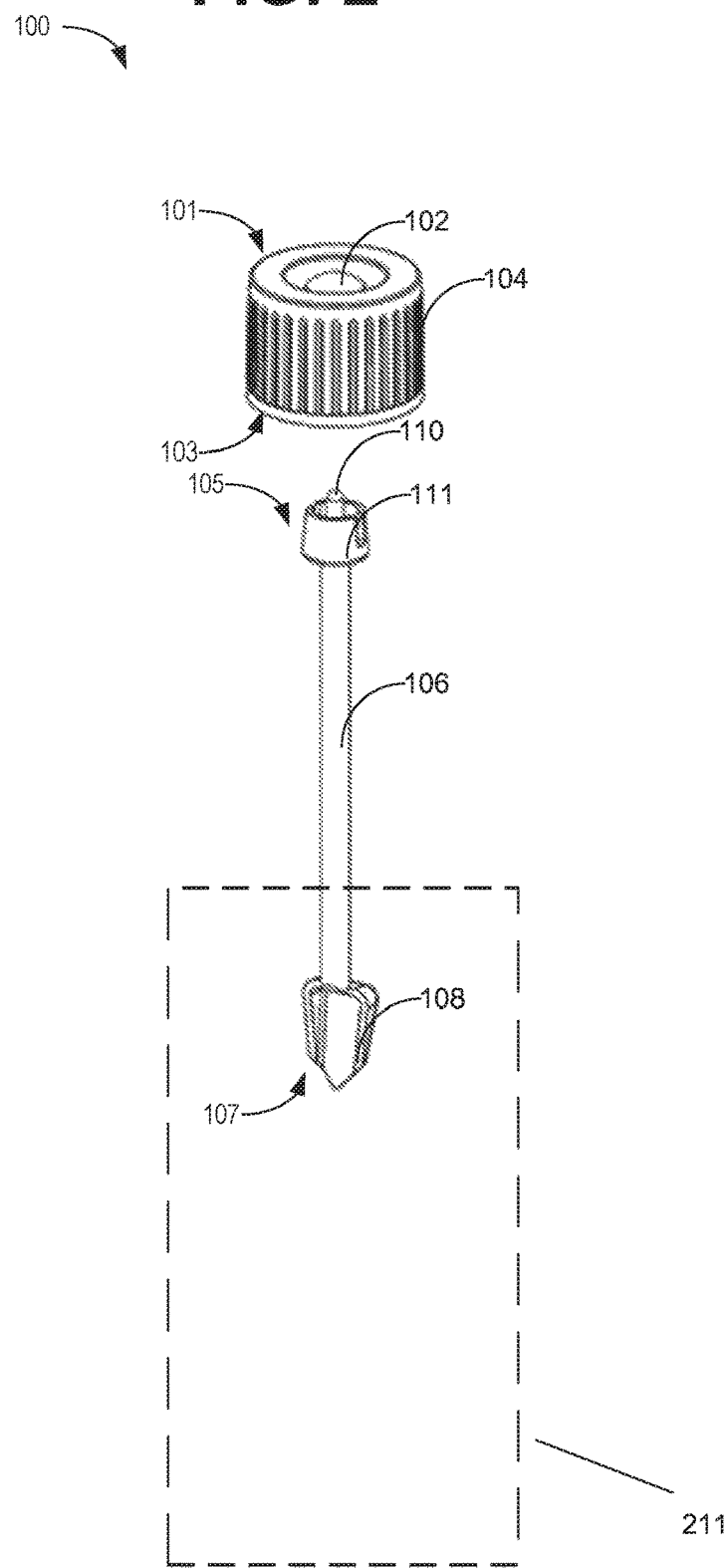
FIG. 2 is a perspective view of a sample collection apparatus with a cap and a releasable sample collection device.
Figure 3:
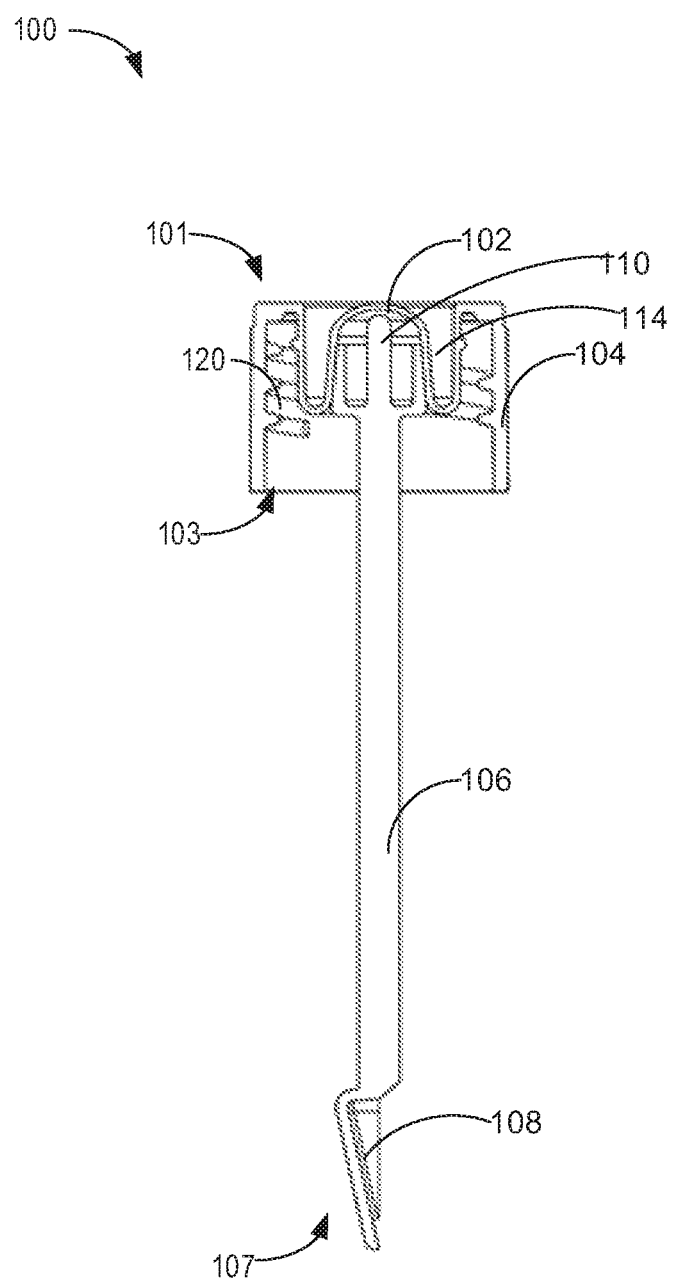
FIG. 3 is a cross-sectional view of the sample collection apparatus of FIG. 1.
Figure 4:
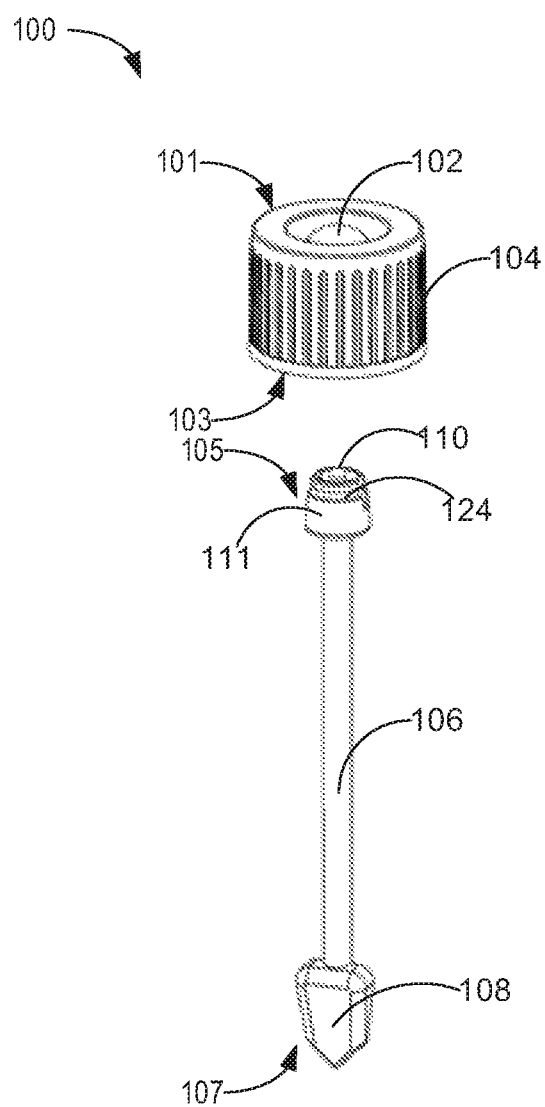
FIG. 4 shows a perspective view of an embodiment of a sample collection apparatus.
Figure 5:
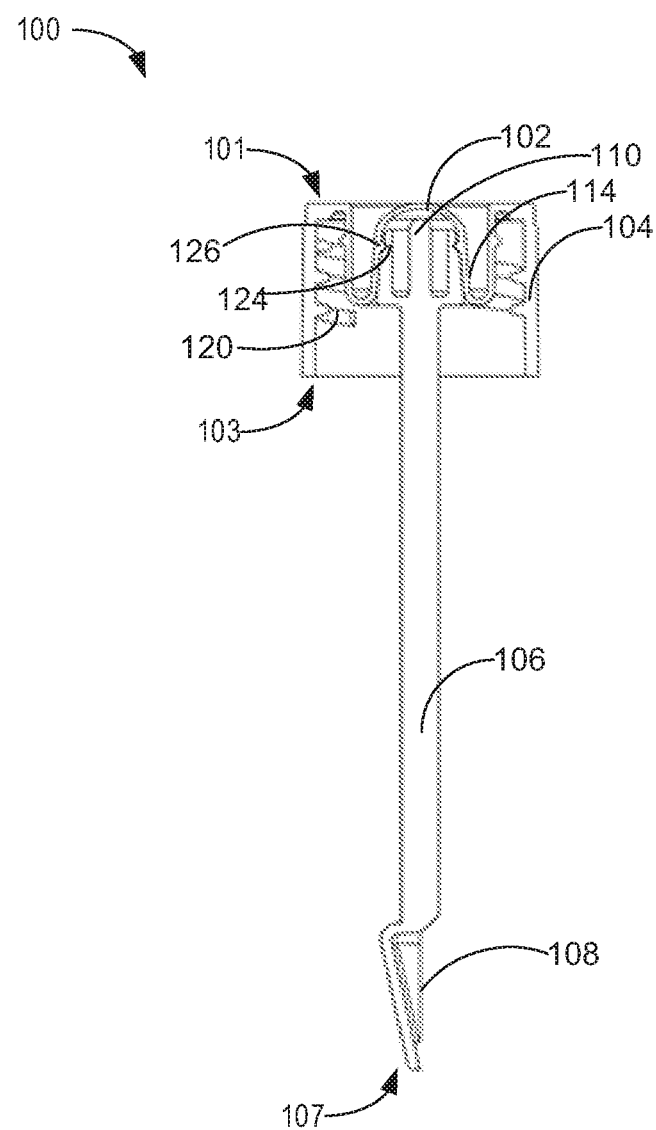
FIG. 5 is a cross-sectional view of the sample collection apparatus of FIG. 4.
Figure 6:
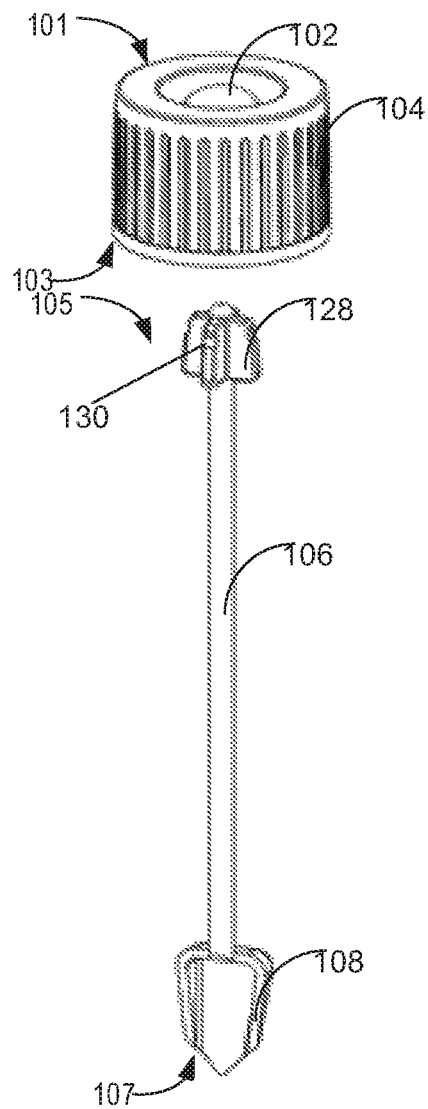
FIG. 6 shows an embodiment of a sample collection apparatus.
Figure 7:
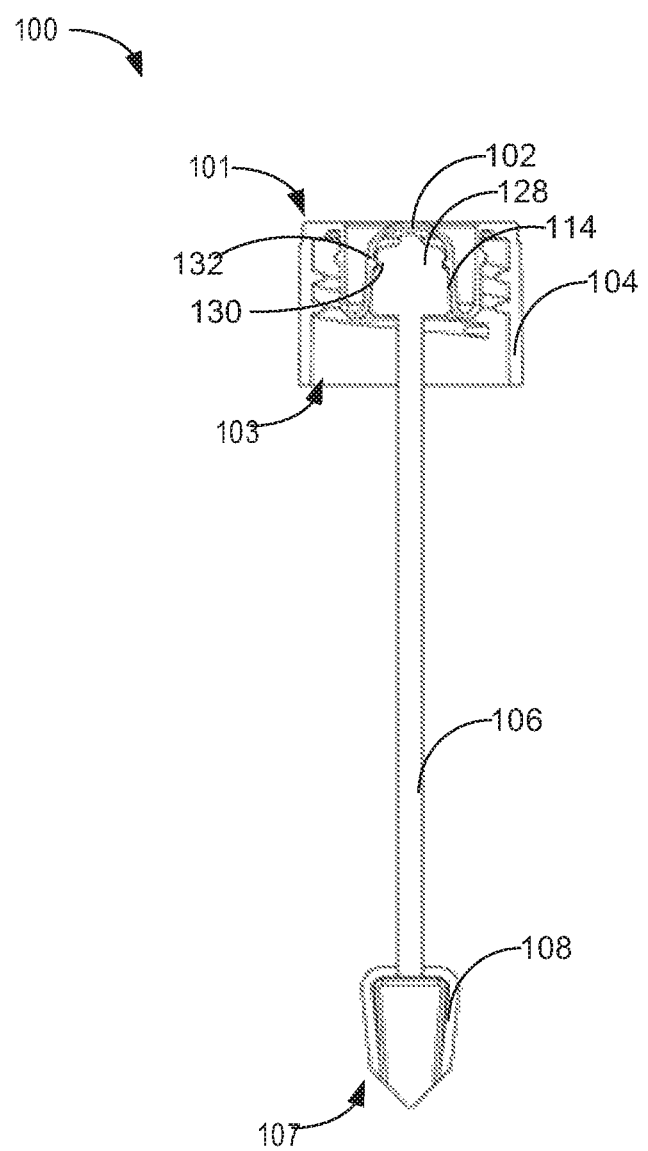
FIG. 7 shows a cross-sectional view of the sample collection apparatus of FIG. 6.
Figure 8:
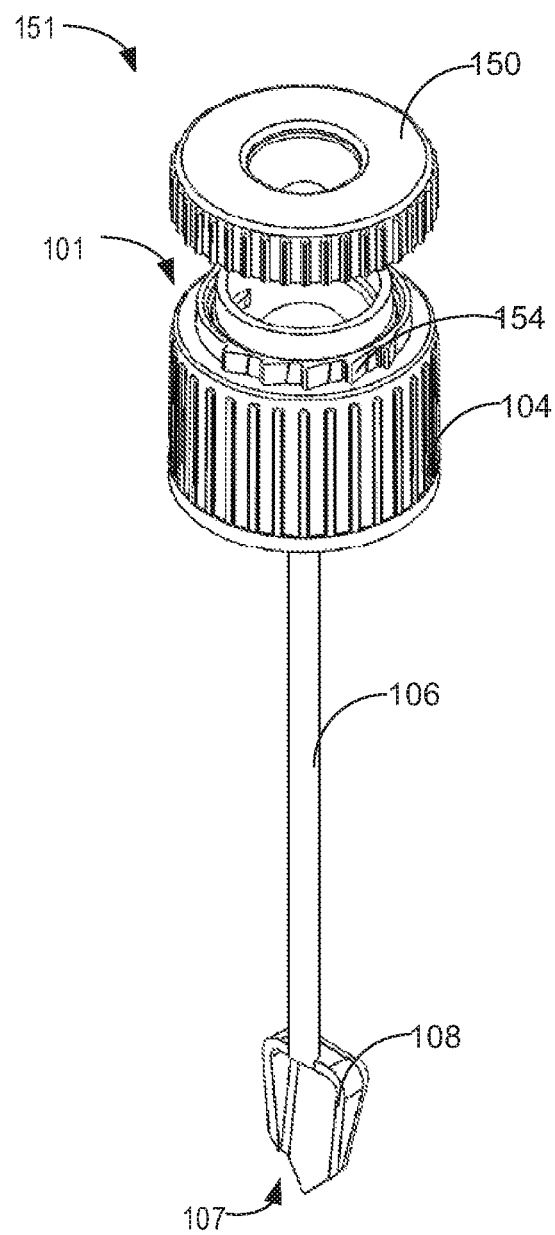
FIG. 8 shows a perspective view of an embodiment of a sample collection apparatus.
Figure 9:
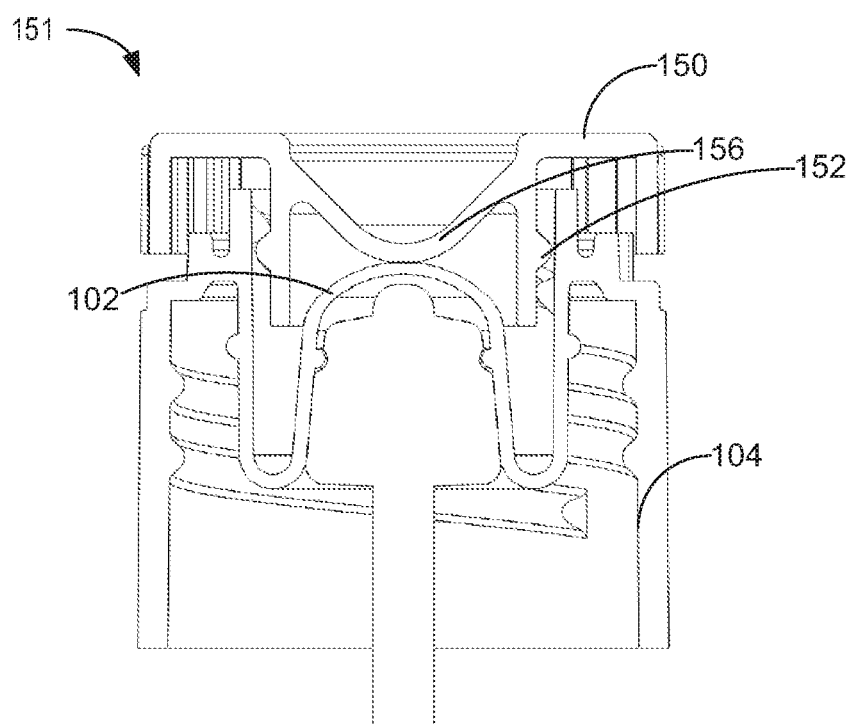
FIG. 9 shows a cross-sectional view of the sample collection apparatus of FIG. 8.
Figure 10:
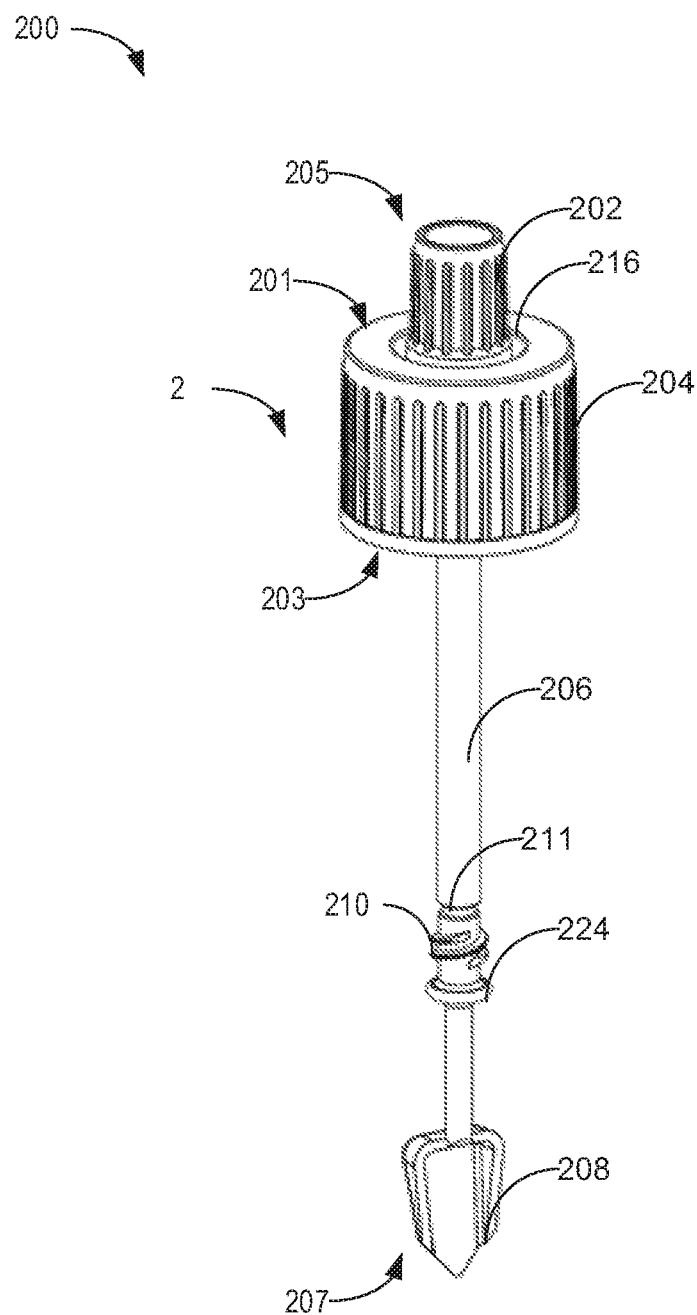
FIG. 10 is a perspective view of a sample collection device coupled to the cap in a first position.
Figure 11:
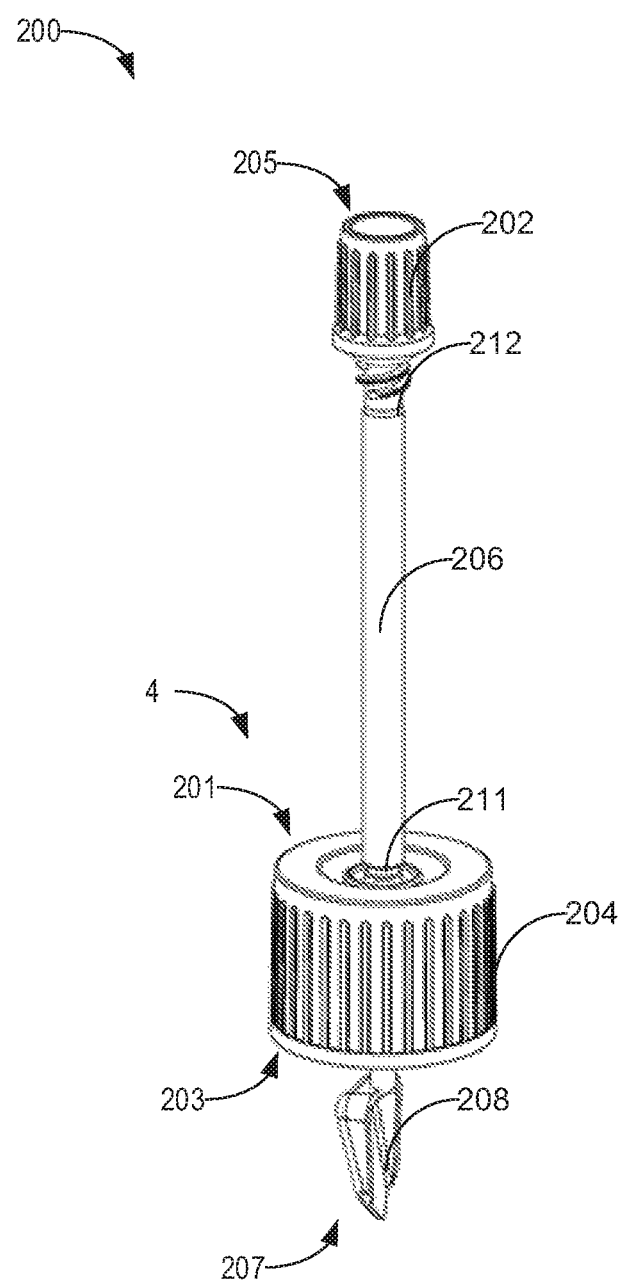
FIG. 11 is a perspective view of a sample collection device coupled to a cap in a second position.

The present application relates to a biological sample collection apparatus. The sample collection apparatus may include a sample collection device configured to couple to a cap. The sample collection device may couple to the cap through a first end of the sample collection device. FIGS. 1-3 show an embodiment of the sample collection apparatus with a sample collection device coupled to a cap. The coupling mechanism includes a socket in the cap receiving and securing the sample collection device in an underside of the cap. The sample collection device may be released from the cap through a manual eject mechanism. FIGS. 4 and 5 show another embodiment of a sample collection device coupled to a cap through a notch on the sample collection device engaging with a complementary raised element on the underside of the cap. FIGS. 6 and 7 show a sample collection device with a tapered rib and notch to engage with a socket on the cap underside. FIGS. 8 and 9 show another embodiment of a sample collection apparatus. FIGS. 10-11 show a sample collection apparatus with a cap coupling to a sample collection device at two different positions on a shank of the sample collection device. Additionally, a part of the sample collection device may be releasable from the cap. The embodiments illustrated in FIGS. 1-13 are drawn approximately to scale, although various modifications in the relative sizing of one or more components may be made. FIG. 14 describes an example method using the sample collection apparatus for sample collection.

FIGS. 1-7 illustrate a non-limiting example of a sample collection apparatus 1. For purpose of discussion, the FIGS. 1-7 will be discussed collectively. The sample collection apparatus 100 may include a cap 104 with a cap top side 101 and a cap underside 103, opposite the cap top side 101. The sample collection device 100 may also include a sample collection shank 106 with a shank first end 105 and a shank second end 107, opposite the shank first end 105.

The sample collection apparatus 100 may include the sample collection shank 106 terminating in a scoop 108 on the shank second end 107. The sample collection shank 106 ending in the scoop 108 may function as a mechanism for sample collection. In other examples, the sample collection shank 106 may terminate in a spoon, a fork, a spatula, or a sample retaining form to enable sample collection. In one embodiment, the sample collection device 106 may be only a shank without any sample retaining form.

The sample collection shank first end 105 may include a coupling mechanism to couple the shank 106 to the cap 104. The coupling mechanism may function to reversibly couple and secure the shank 106 to the cap 104. In one example, the sample collection shank first end 105 may be received in the cap underside 103 and may be reversibly secured to the cap underside 103. In one embodiment, the shank first end 105 may be tapered element 110. In another example, the shank first end 105 may include a cylindrical element 111 around the tapered element 110. The tapered element 110 along with the cylindrical element 111 at the shank first end 105 may couple to a complementary socket 114 at the cap underside 103, as illustrated in FIG. 3. The tapered element 110 along with the cylindrical element 111 at the shank first end 105 may form a reversible tight fit with the cap socket 114, securing the cap 102 and the shank 106. The coupling mechanism may include other means of reversible coupling, described below with reference to embodiments shown in FIGS. 4-6.

The cap 104 may include the cap top side 101 and the cap underside 103. The cap top side 101 may include a release mechanism to release the sample collection device shank 106 from the cap underside. In one example, the release mechanism may include a flexible dome 102. The flexible dome 102 may be located at the center of the cap top side 101 and may function as a release mechanism to release the shank first end 105 inserted into the complementary socket 114 at the cap underside 103. The flexible dome 102 top surface may be pressed downwards towards the cap underside 103 by applying pressure on top of the flexible dome 102. In one example, the flexible dome 102 at the cap top side 101 may have a convex curvature and upon application of pressure on the flexible dome 102 top surface, the top surface may become less convex, flatter, or concave, depending on the amount of pressure applied and the flexibility of the dome surface. As the flexible dome 102 changes from convex to concave upon application of pressure on the flexible dome 102 top surface, the associated bottom surface of the dome 102 may change from concave to convex on the cap underside 103, thereby acting as a mechanism for pushing out the shank first end 105 inserted inside the complementary socket 114 on the cap underside 103.

In another example, the release mechanism may include an additional mechanical actuator 150 on top of the cap 104, as illustrated in the embodiment 151 in FIGS. 8 and 9. The mechanical actuator 150 may include threads 152 and a rounded projection 156. The mechanical actuator 150 may also snap onto the top of the cap 104. As the mechanical actuator 150 is screwed or pressed downward onto the top of the cap 104, the rounded projection 156 may apply pressure on the flexible dome 102, pushing out the shank first end 105 and releasing the shank 106 from the cap 104. The mechanical actuator may include a ratcheting feature 154 to prevent loosening and accidental removal of the actuator. In further examples, a release actuator may be present on the sample collection device.

The cap 104 may be configured to couple to a standard specimen jar or tube, used for collecting biological samples. The cap 104, coupling to the specimen jar may secure the contents of the specimen jar for storing, and during transportation. In one example, the cap may include mating threads 120 inside the cap 104, as shown in FIG. 3. The mating threads 120 inside the cap 104 may couple the cap to a standard specimen jar by reversible mating of threads 120 to complementary threads present on the specimen jar.

The cap 104 may also include a gripping surface 122 on the cap 104. In one example, the gripping surface may include parallel ridges that may enable easy gripping and handling of the cap 104 during coupling and uncoupling of the cap from the specimen jar. In other examples, the gripping surface may include surfaces providing adequate friction to enable easy gripping of the cap 104 during handling.

Referring to FIGS. 4 and 5, an embodiment of the sample collection apparatus 100 is shown where the coupling mechanism of the shank first end 105 with the cap underside 103 includes a notch 124 encircling the shank first end 105. The notch 124 may be positioned along the circumference of the cylindrical element 111. In one example, the notch 124 may be present in only part of the circumference of the cylindrical element 111. In another example, more than one notch may be present along the shank first end 105. The notch 124 may function as a securing mechanism coupling the shank 106 to the cap 104. In one example the shank first end 105, inserting into the socket 114 at the cap underside 103 may include the notch 124 forming an interlocking face sharing contact with a complementary ring 126 inside the socket 114 at the cap underside 103, thereby securing the shank 106 to the cap 104. In one example, more than one complementary interlocking notches and rings may be present on the shank first end 105 and the socket 114 on the cap underside 103. In one example, the release of the shank first end 105 from the cap underside may be by pushing the flexible dome 102 top surface at the cap top side 101, thereby ejecting the cylindrical element 111 with the notch 124 from the socket 114 at the cap underside 103.

FIGS. 6 and 7 show another example of a mechanism coupling the shank first end 105 to the cap underside 103. A tapered rib 128 may be present on the shank first end 105. The tapered rib 128 may include a plurality of ridges, for example, four ridges along the tapered rib 128. In other examples, more or less ridges may be present along the tapered rib. The tapered rib 128 may also include a notch 130 running along the circumference of the tapered rib 128. The tapered rib 128 at the shank first end 105 may insert into the socket 114 at the cap underside 103 to form a face-sharing contact securing the shank to the cap. In one example, the notch 130 on the tapered rib may form an interlock with a complementary ring 132 inside the socket 114. The release of the shank first end 105 from the cap underside may be by pushing the flexible dome 102 top surface at the cap top side 101, thereby ejecting the tapered rib 128 with the notch 130 from the socket 114 at the cap underside 103.

FIGS. 10-13 show another embodiment of a sample collection apparatus 200, wherein a cap 204 may couple to a sample collection shank 206. The coupled sample collection shank 206 may be adjustable in relation to the cap 204 in a first position 2 or in a second position 4.

The shank 206 may include a shank first end 205 and a shank second end 207, opposite the shank first end 205. The shank first end 205 may include a shank knob 202. The shank knob 202 may function to secure the cap 204 to the shank first end 205 and may function as a gripping surface for handling the shank 206 during sample collection. The knob 202 may be reversibly coupled to the shank first end 205. In one example, the knob 202 may be coupled to the shank first end 205 by mating of complementary screw threads between the knob 202 and the shank first end 205. The shank second end 207 may terminate in a sample collection form, for example a scoop 208, as illustrated in FIG. 10. In other examples, the shank second end 207 may terminate in a spoon, a fork, or a spatula.

Figure 12:
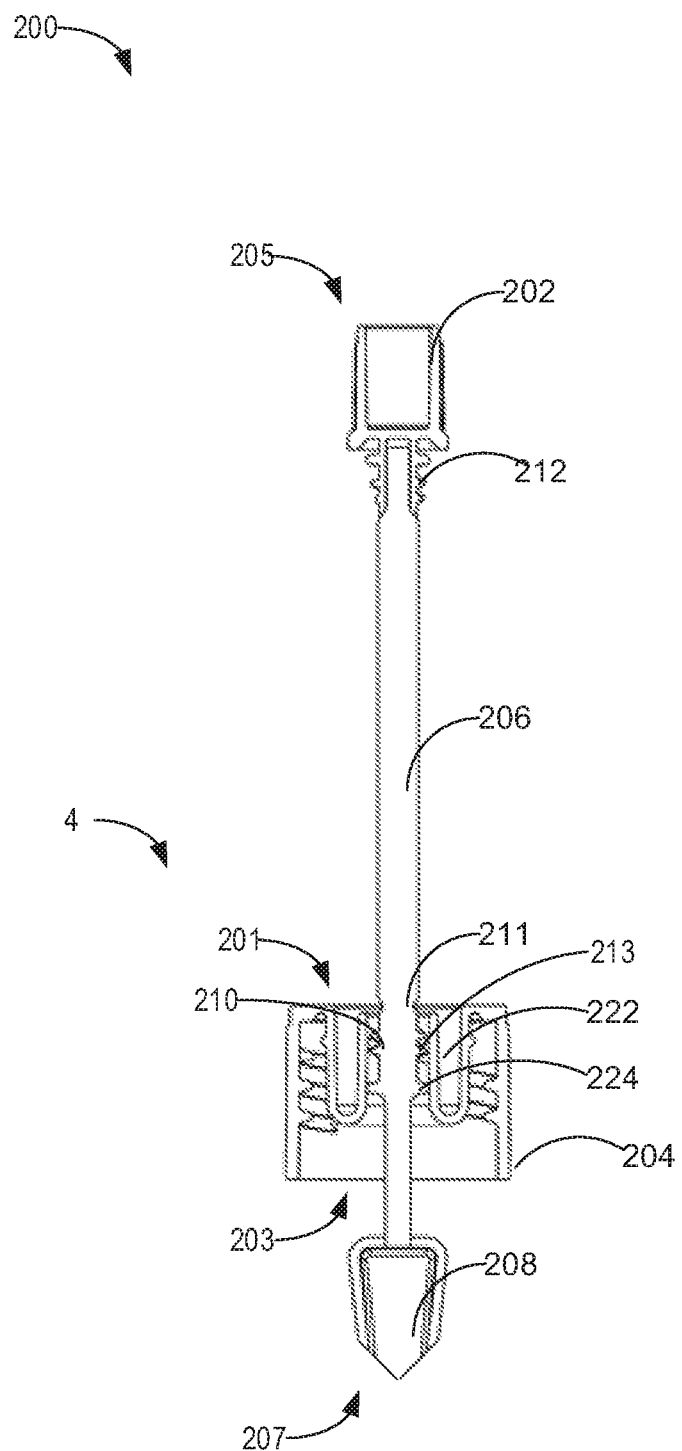
FIG. 12 shows a cross-sectional view of the sample collection apparatus of FIG. 11.

Along the length of the shank 206 there may be a shank first threaded section 212 and a shank second threaded section 210, as illustrated in FIGS. 10-12. The threaded sections may function to couple the cap 204 to the shank 206, as will be described in details below. The first threaded section 212 may be towards the shank first end 205. In one example, the first threaded shank may be adjoining the base of the knob 202. The second threaded section 210 may be closer to the shank second end 207. In other examples, the position of the first threaded section 212 and the second threaded section 210 along the shank 206 may vary. In other examples, additional threaded sections may be present on the shank 206 to adjust the position of the cap along the sample collection device.

The shank 206 may include a cutaway portion 211. The cutaway portion 211 may function as a point for breaking off the shank 206. In one example illustrated in FIG. 10, the cutaway portion 211 is adjoining the second threaded section 210 of the shank 206. In one example, the circumference of the shank 206 at the cutaway portion 211 may be less than the remainder of the shank 206, conducive for breaking the shank at the cutaway portion 211. In other examples, more than one cutaway portion may be present along the length of the shank 206. When the sample collection shank 206 is in the second position 4, the cutaway portion 211 may be positioned above a top side 201 of the cap 204. In another example, the cutaway portion 211 may be adjoining the top side 201 of the cap 204, as illustrated in FIG. 11.

The shank 206 may be configured to pass through the cap 204 and couple to the cap along the length of the shank 206, as illustrated in FIGS. 10-13. The cap 204 may include the cap top side 201 and a cap underside 203. The cap 204 may include a hole 216 capable of accommodating the shank 206 passing through the hole 216 from the cap underside 203 to the cap top side 203. The shank knob 202 may be uncoupled from the shank first end 205 and the shank 206 first end may be passed through the hole 216 from the cap underside to the cap top side. The knob 202 may be attached back to the shank first end 205, after the shank has been passed through the cap 204.

The cap 204 may couple to the shank 206 passing through the cap 204, at the first position 2, such that the cap reversibly couples to the threaded section 212, adjoining the knob 202 at the shank first end 205, as illustrated in FIG. 10. FIG. 11 shows the cap 204 may also reversibly couple to the shank 206 at the second position 4 at the second threaded section 210 on the shank 206. The coupling of the cap to the shank at the first position 2 and at the second position 4 may be by reversible mating of complementary threads 213 inside the cap 204 with the threads on the shank first threaded section 212 or the shank second threaded section 210. In other examples, there may be additional positions along the shank 206 where the cap 204 may couple to the shank 206.

Referring to FIG. 12, the cap 204 is shown coupled to the shank 206 at the second position 4. The mating threads 213 inside the cap may reversibly mate with the shank threaded section 210. The shank 206 may pass through a complementary socket 222 in the cap 204, forming a face-sharing contact between the shaft 206 and the complementary socket 222. A sealing ring 224, adjacent to the shank second threaded section 210, may form a liquid tight fit between the shank 206 and the cap 204, coupled in the second position 4. The cutaway portion of the shank 206 may be adjacent to the cap top side when the cap is coupled to the shank in the second position. Similarly, when the cap is coupled to the shank in the first position, the mating threads of the cap 204 may secure the cap by reversible mating with the shank first threaded section 212. The complementary socket 222 of the cap 204 may be in face sharing contact with the shank 206 coupled to the cap 204 in the first position 2. The shank may be moved from the first position 2 to the second position 4 by unscrewing the cap from the shank first threaded section 212 and moving the shank upwards to screw the cap with the shank second threaded section 210. Conversely, the shank may be moved from the second position to the first position. The threads 213 may be shaped such that they contact the shank 206 and wipe clean any residual sample materials as the shank 206 is moved through the complementary socket 222.

Figure 13:
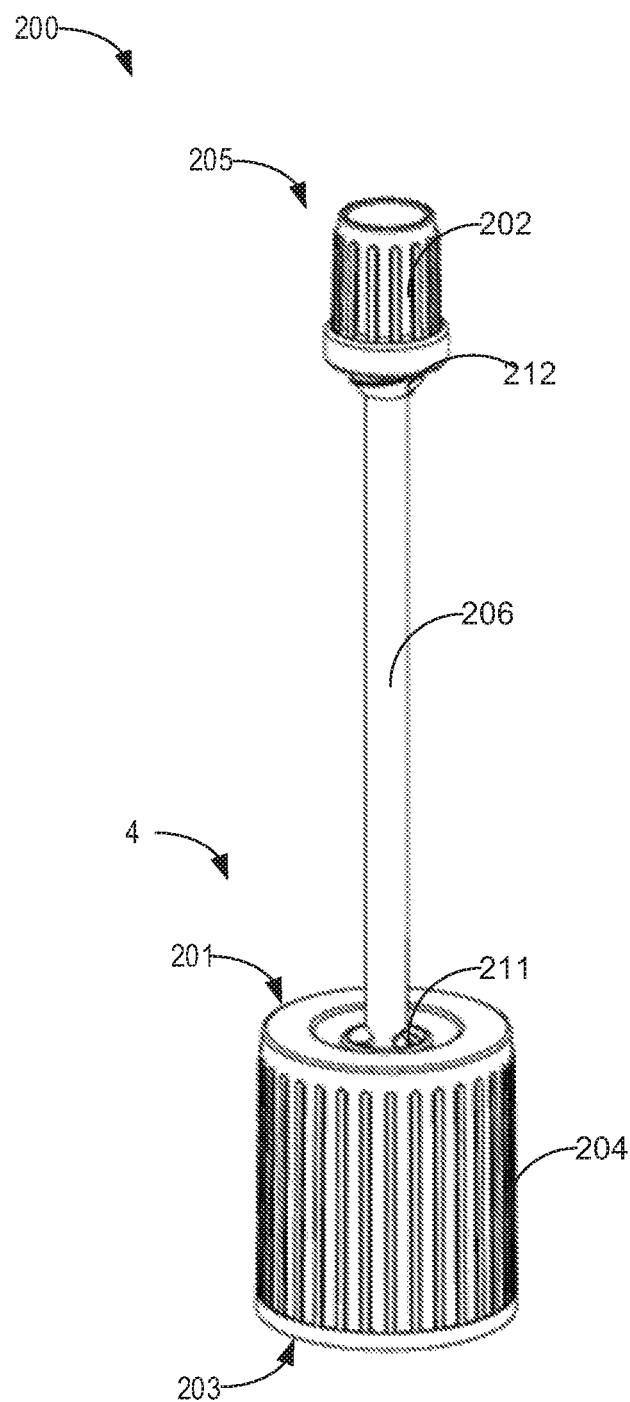
FIG. 13 shows a perspective view of an embodiment of a sample collection apparatus.
Figure 14:
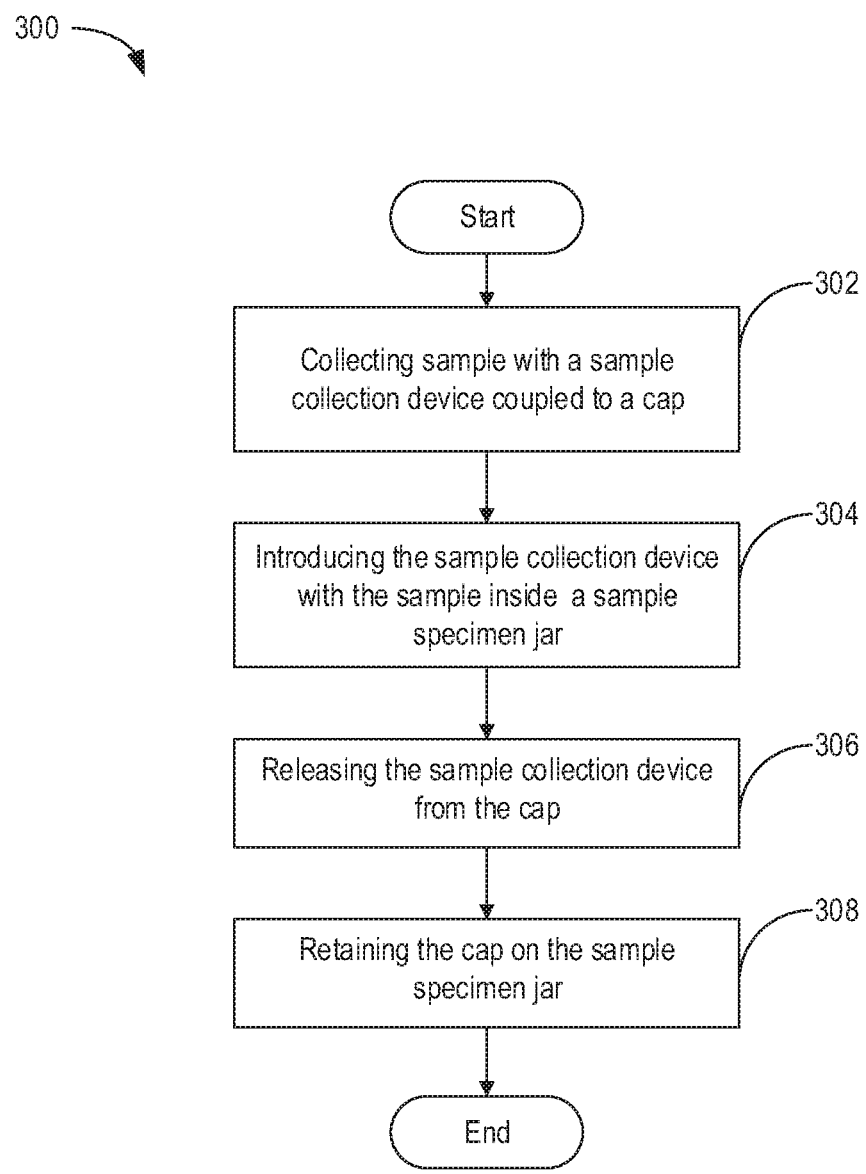
FIG. 14 shows an example method using a sample collection apparatus with a releasable sample collection device coupled to a cap.

FIG. 13 illustrates coupling of the cap 204 with the shank 206 in the second position 4, such that the cap 204 may extend to shroud the shank second end 207. The cap shrouding the scoop may acts as a means of restricting residual sample on the scoop from contaminating the contact environment. In one example, the cap 204 may shroud the scoop completely when the length of the cap extends to cover the scoop. In other example, the scoop may be partly shrouded by the cap coupled in the second position. The position of the shank second threaded section 210 in relation to the scoop 208 on the shank 206 may also determine the extent of the scoop that may be shrouded by the cap coupled to the second threaded section 210. For example, the scoop may not be shrouded at all, the scoop may be partially shrouded, or the scoop may be completely shrouded by the cap coupled to the shank threaded section 210.

The shank 206 coupled to the cap 204 may be released from the cap 204 by breaking the shank 206 at the cutaway portion 211 of the shank 206. In one example, when the cap is coupled to the shank 206 in the second position, the extended shank 206 upwards of the cap topside 201 may be broken off at the cutaway portion 211 adjoining the top side 201 of the cap 204. In another example, more than one cutaway portion may be present along the shank 206, releasing various segments of the shank coupled to the cap.

FIG. 14 illustrates an example method 300 of using the sample collection apparatus 100 or 200. The sample being collected may be a biological sample, such as fecal material. In another example, the biological sample may be a tissue. In yet another example, the sample may be mucous discharge. The biological sample may be of human origin. In other examples, the biological sample may be of animal origin or plant origin. The sample collection device may include a sample collection shank with a shank coupled to a cap. The cap may reversibly couple to standard sample specimen jars 211.

The method 300 starts at 302, collecting the sample with the sample collection apparatus. In one example, the sample collection apparatus may include a cap coupled to a sample collection device. The sample collection device may include a shank terminating in a scoop. The sample may be collected using the scoop at the end of the shank, as the scoop 108 or the scoop 208 illustrated in FIGS. 1 and 10, respectively. The cap may function as a gripping surface for handling the sample collection apparatus. A coupling mechanism may secure the cap to the sample collection device. In one example, the coupling mechanism may include a socket on a cap underside receiving a complementary portion of the sample collection device.

After collecting the sample, the method 300 proceeds to 304, introducing the sample collection apparatus with the sample into a sample specimen jar. The sample specimen jar receiving the sample on the sample collection apparatus may include a collection and/or processing liquid for storing and/or processing the sample. In one example, the fluid may be a fixative. In other examples, the fluid may be a diluent, such as water or saline. The cap coupled to the sample collection shank may be coupled to the sample specimen jar. The sample may be stored and/or transported in the sample specimen jar with the sample collection device attached to the cap coupled to the sample specimen jar.

The method 300 proceeds to 306, releasing the sample collection device from the cap. The sample collection device may be released inside the sample specimen jar, without uncoupling the cap. The sample collection device may be released outside the sample specimen jar, for example in a waste collection bin, after uncoupling the cap from the sample specimen jar. In one example, the position of the sample collection device coupled to the cap may be changed, for example, the sample collection device may be moved from a first position to a second position, as described above with reference to FIGS. 10-13. In one example, only a part of the sample collection device may be released from the cap when the sample collection device is in the second position, as illustrated in FIG. 11. In another example, the complete sample collection device may be released, for example in embodiments illustrated in FIGS. 1, 4, 6, and 8. The displacement of the sample collection device from the cap and discarding the displaced sample collection device minimizes contamination risk during sample retrieval from the sample specimen jar.

The releasing of the sample collection device from the cap at 306 may be carried out by a displacement mechanism. In one example, the displacement mechanism may include a mechanical actuator on the cap top surface releasing the coupled sample collection device from the cap underside. In another example, a cutaway portion on the sample collection device may act as a mechanism to displace a portion of the sample collection device from the cap.

After releasing the sample collection device from the cap, the method 300 may proceed to 308, retaining the cap on the sample specimen jar. Retaining the cap on the sample specimen jar may secure the contents of the sample specimen jar for storage and/or transport. The retaining of the cap may include coupling of complementary threads inside the cap with complementary threads on an open end of the specimen jar. In other example, the cap may be secured to the sample specimen jar by other means of coupling, including, but not limited to a twist-lock mechanism of coupling.

Thus, the embodiments of the above described sample collection apparatus with a releasable sample collection device coupled to a cap, configured to couple to a sample specimen jar, may reduce the risk of contamination from dripping of biological sample from the sample collection device. After introducing a sample collected by the sample collection device coupled to a cap into a sample specimen jar, at least a part of the sample collection device may be discarded by releasing it from the cap, and the cap may be secured to the sample specimen jar for storage and/or transport of the collected sample.

In one embodiment, a biological sample collection apparatus may include a cap and a sample collection device having a first configuration and a second configuration, where in the first configuration the sample collection device is coupled to the cap and in the second configuration, at least a portion of the sample collection device is released from the cap. A coupling mechanism positions the sample collection device in the first configuration. The coupling mechanism may include includes at least one threaded portion on the sample collection device mating with a complementary threaded portion on the cap. In another example, the coupling mechanism may include a socket in the cap receiving the sample collection device. In one embodiment, a displacement mechanism may position the sample collection device in the second configuration.

In one example, the displacement mechanism may include a mechanical actuator on the cap. In another example, the displacement mechanism may include a cutaway portion on the sample collection device. The sample collection device may include a shank terminating in a scoop.

In another embodiment, a biological sample collection apparatus may include a cap, a sample collection device with a shank terminating in a scoop, the shank coupled to the cap, and a release actuator to release at least a part of the sample collection device from the cap. In an example, the release actuator may be a mechanical actuator on the cap. In another example, the release actuator may be a cutaway portion on the shank of the sample collection device.

In another example, the sample collection device coupled to the cap may be adjustable to a first position and a second position relative to cap, where in the first position the cap may be spaced apart from the cutaway portion of the sample collection device and in the second position the cutaway portion of the sample collection device may be positioned above a top side of the cap. In an example, the cutaway portion is adjoining the top side of the cap when the sample collection device is in the second position. In one embodiment, when the sample collection device in the second position, the cap may shroud at least a portion of a sample collection end of the sample collection device. In one example, at least a portion of the sample collection device may be released from the cap when the sample collection device is in the second position.

An example method for collecting biological sample using a sample collection apparatus, may include collecting a sample using a sample collection device coupled to a cap, introducing the sample collection device with the sample into a sample specimen jar, releasing the sample collection device from the cap and retaining the cap on the sample specimen jar. In one example, the method may include releasing only a portion of the sample collection device from the cap. In another example, releasing the sample collection device from the cap may be done after coupling the cap to the sample specimen jar. In an example, releasing the sample collection device from the cap may be done outside the sample specimen jar.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A biological sample collection apparatus, comprising:
a cap; and
a sample collection device having a first configuration and a second configuration, where in the first configuration the sample collection device is coupled to the cap and in the second configuration at least a portion of the sample collection device is released from the cap,
wherein a coupling mechanism positions the sample collection device in the first configuration, and a displacement mechanism positions the sample collection device in the second configuration,
the coupling mechanism and the displacement mechanism arranged within the cap.

2. The biological sample collection apparatus of claim 1, wherein the coupling mechanism includes at least one threaded portion on the sample collection device mating with a complementary threaded portion on the cap.

3. The biological sample collection apparatus of claim 1, wherein the coupling mechanism includes a socket in the cap receiving the sample collection device.

4. The biological sample collection apparatus of claim 1, wherein the displacement mechanism includes a mechanical actuator on the cap.

5. The biological sample collection apparatus of claim 1, wherein the displacement mechanism includes a cutaway portion on the sample collection device.

6. The biological sample collection apparatus of claim 1, wherein the sample collection device includes a shank terminating in a scoop.

7. The biological sample collection apparatus of claim 1, wherein the sample collection device coupled to the cap is adjustable to a first position for sample collection and a second position relative to the cap, where in the first position the cap is spaced apart from a cutaway portion of the sample collection device and in the second position the cutaway portion of the sample collection device is positioned above a top side of the cap.

8. The biological sample collection apparatus of claim 7, wherein the cutaway portion is adjoining the top side of the cap when the sample collection device is in the second position.

9. The biological sample collection apparatus of claim 7, wherein, when the sample collection device is in the second position, the cap shrouds at least a portion of a sample collection end of the sample collection device.

10. The biological sample collection apparatus of claim 7, wherein at least a portion of the sample collection device is released from the cap when the sample collection device is in the second position.

11. A method for collecting a biological sample using a sample collection apparatus, comprising:
collecting a sample using a sample collection device coupled to a cap via a coupling mechanism;
introducing the sample collection device with the sample into a sample specimen jar;
releasing the sample collection device from the cap via a displacement mechanism; and
retaining the cap on the sample specimen jar,
wherein the coupling mechanism and the displacement mechanism are arranged in an underside of the cap.

12. The method of claim 11, further comprising releasing only a portion of the sample collection device from the cap.

13. The method of claim 11, further comprising releasing the sample collection device from the cap after coupling the cap to the sample specimen jar.

14. The method of claim 11, further comprising releasing the sample collection device from the cap outside the sample specimen jar.

15. A biological sample collection apparatus, comprising:
   a cap;
   a sample collection device with a shank terminating in a scoop, the shank coupled to the cap; and
   a release actuator to release at least a part of the sample collection device from the cap,
   wherein the release actuator is arranged on the cap.

16. The biological sample collection apparatus of claim 15, wherein the release actuator is a mechanical actuator on the cap.

17. The biological sample collection apparatus of claim 15, wherein the release actuator is a cutaway portion on the shank of the sample collection device.

18. The biological sample collection apparatus of claim 15, wherein the cap is configured to couple to a specimen jar.

* * * * *